(12) United States Patent
Shaker et al.

(10) Patent No.: US 11,213,454 B1
(45) Date of Patent: Jan. 4, 2022

(54) METHOD TO PROVIDE REAL-TIME FEEDBACK AND COACHING TO AUGMENT CARDIAC RESCUE

(71) Applicant: ALTRIX MEDICAL, INC., Centreville, VA (US)

(72) Inventors: Matthew Robert Shaker, Centreville, VA (US); Daniel Fleck, Potomac, MD (US)

(73) Assignee: Altrix Medical, Inc., Centreville, VA (US)

( * ) Notice: Subject to any disclaimer, the term of this patent is extended or adjusted under 35 U.S.C. 154(b) by 0 days.

(21) Appl. No.: 17/339,979

(22) Filed: Jun. 5, 2021

(51) Int. Cl.
*A61H 31/00* (2006.01)
*G06T 7/20* (2017.01)
*A61N 1/39* (2006.01)

(52) U.S. Cl.
CPC ......... *A61H 31/005* (2013.01); *A61H 31/007* (2013.01); *A61N 1/39044* (2017.08); *A61N 1/3993* (2013.01)

(58) Field of Classification Search
CPC .... A61H 31/00; A61H 31/004; A61H 31/005; A61H 31/007; A61H 31/008; G01B 11/14; G01B 11/026; G06T 7/74; G06T 2207/10028; G06T 7/20; G06T 7/70; G06T 7/254; G06T 7/521; G06T 7/579
See application file for complete search history.

(56) References Cited

U.S. PATENT DOCUMENTS

| | | |
|---|---|---|
| 6,321,113 B1 | 11/2001 | Parker et al. |
| 7,262,747 B2 | 8/2007 | Ebersole et al. |
| 8,979,764 B2 | 3/2015 | Elghazzawi et al. |
| 9,026,147 B2 | 5/2015 | Galvin et al. |
| 9,576,502 B2 | 2/2017 | Griesser et al. |
| 10,335,574 B2 | 7/2019 | Tegg et al. |
| 10,335,604 B2 | 7/2019 | Gehman et al. |
| 2004/0015191 A1* | 1/2004 | Otman ............. A61N 1/3925 607/5 |

(Continued)

OTHER PUBLICATIONS

Minami et al., Real time auto feed back system for chest compressions using an infrared camera, 2013, Resuscitation 84 e137-e138 (Year: 2013).*

(Continued)

*Primary Examiner* — Timothy A Stanis
*Assistant Examiner* — Christopher E Miller
(74) *Attorney, Agent, or Firm* — Louis Ventre, Jr.

(57) ABSTRACT

A method to provide real-time feedback and coaching to augment cardiac rescue by a rescuer. The rescuer would typically be attempting cardiopulmonary resuscitation (CPR) or administering an electrical shock from a defibrillator. The method includes steps of providing a computer, a data-generation device, a cuing device, using the data-generation device, and activating the cuing device. Optional steps include: attaching an article to the rescuer, providing a stationary component, using the camera to provide data to the computer; recording data from the use of a defibrillator; and combining data from the use of a defibrillator and the data on a rate of cardio pulmonary resuscitation and depth of chest compression by the rescuer with video data from the camera to produce combined data, which will be available for after-action review.

13 Claims, 6 Drawing Sheets

(56) References Cited

U.S. PATENT DOCUMENTS

| | | | | |
|---|---|---|---|---|
| 2008/0312565 | A1* | 12/2008 | Celik-Butler | A61H 31/007 601/43 |
| 2011/0040217 | A1* | 2/2011 | Centen | G06T 7/60 601/41 |
| 2012/0136286 | A1* | 5/2012 | Nova | A61H 31/007 601/41 |
| 2012/0184882 | A1* | 7/2012 | Totman | A61H 31/004 601/41 |
| 2014/0066822 | A1* | 3/2014 | Freeman | A61H 31/006 601/41 |
| 2014/0342331 | A1* | 11/2014 | Freeman | A61H 31/005 434/265 |
| 2015/0045697 | A1* | 2/2015 | Richard | A61H 31/005 600/587 |
| 2015/0087919 | A1* | 3/2015 | Johnson | G16H 20/40 600/301 |
| 2015/0164417 | A1* | 6/2015 | Tupin, Jr. | A61B 5/0205 600/407 |
| 2015/0179219 | A1* | 6/2015 | Gao | G06T 7/254 386/278 |
| 2015/0351647 | A1* | 12/2015 | Dantu | A61B 5/6824 601/41 |
| 2016/0128626 | A1* | 5/2016 | Johnson | G16H 20/40 600/301 |
| 2016/0143804 | A1* | 5/2016 | Nilsson | A61H 31/006 601/41 |
| 2017/0105898 | A1* | 4/2017 | Taylor | G06T 7/0012 |
| 2017/0156977 | A1* | 6/2017 | Walden | A61H 31/006 |
| 2017/0181925 | A1* | 6/2017 | Oppenheimer | G06F 1/163 |
| 2017/0196767 | A1* | 7/2017 | Cox | A61B 5/024 |
| 2017/0273864 | A1* | 9/2017 | Kaufman | A61H 31/005 |
| 2017/0281461 | A1* | 10/2017 | Kokubo | A61H 31/005 |
| 2018/0040255 | A1* | 2/2018 | Freeman | A61H 31/00 |
| 2018/0092802 | A1* | 4/2018 | Giacometti | A61H 31/005 |
| 2018/0147113 | A1* | 5/2018 | Dellimore | G16H 40/67 |
| 2018/0174489 | A1* | 6/2018 | Dellimore | A61B 5/0077 |
| 2019/0066538 | A1* | 2/2019 | Chao | A61N 1/3993 |
| 2019/0133879 | A1* | 5/2019 | Djajadiningrat | G16H 70/20 |
| 2019/0209871 | A1* | 7/2019 | O'Brien | A61N 5/1075 |
| 2019/0257644 | A1* | 8/2019 | Hillebrand | G01B 11/2518 |
| 2020/0000679 | A1* | 1/2020 | Oppenheimer | A61N 1/3987 |
| 2020/0000680 | A1* | 1/2020 | Silver | A61H 31/005 |
| 2020/0096319 | A1* | 3/2020 | Botero Rosas | A61H 31/00 |
| 2021/0183402 | A1* | 6/2021 | Bharitkar | G10L 21/034 |

OTHER PUBLICATIONS

Digna M González-Otero, et al., Additive Model to Evaluate the Accuracy of Chest Compression, Feedback Systems in Moving Vehicles, Computing in Cardiology 2016; vol. 43 ISSN: 2325-887X DOI:10.22489/CinC.2016.021-218, Bilbao (Spain).

Sofía Ruiz De Gauna, et al., Feedback on the Rate and Depth of Chest Compressions during Cardiopulmonary Resuscitation Using Only Accelerometers, PLOS ONE, DOI:10.1371/journal.pone. 0150139 Mar. 1, 2016, published online at https://www.ncbi.nlm.nih.gov/pmc/articles/PMC4773040/.

* cited by examiner

METHOD TO PROVIDE REAL-TIME FEEDBACK AND COACHING TO AUGMENT CARDIAC RESCUE

TECHNICAL FIELD

In the field of sensing body condition and electrical application for heart-related emergencies, a method is disclosed for improving cardiac rescue utilizing real time feedback.

BACKGROUND ART

Cardiopulmonary resuscitation (CPR) is an emergency procedure that can help save a person's life if their heart stops. The heart is able to pump blood to the brain, the lungs and to other parts of the body because it is triggered by the heart's electrical control system.

Sudden cardiac arrest results when the heart's electrical system malfunctions and causes a person's heart to stop beating. During cardiac arrest, the heart cannot pump blood to the rest of the body, including the brain and lungs. Death can happen in minutes without treatment and cardiopulmonary resuscitation, or CPR, is a preferred treatment that uses chest compressions to mechanically force the heart to pump blood and so help keep blood flowing throughout the body.

Someone in cardiac arrest is experiencing an arrhythmia and should receive CPR as quickly as possible. Arrhythmias are essentially irregular heartbeats. Two types, ventricular fibrillation (VF) and pulseless ventricular tachycardia (pulseless v-tach), can often be reversed using an electrical shock delivered to the heart by a defibrillator if treated promptly, thus giving the heart the opportunity to resume normal contractions in pumping blood.

A challenge with defibrillation is that the electrical shock must be administered very soon after the onset of the arrhythmia. There is not much time to do this since the survival rate decreases by about 10% for each minute the person is in cardiac arrest. After about 10 minutes the rate of survival for SCA victims averages less than 2%.

CPR and defibrillation treatments can be performed by professional first responders or bystanders. No matter who is the rescuer, it would help to have a computerized feedback system that could evaluate the scene and make recommendations to the rescuer for the best outcomes.

SUMMARY OF INVENTION

A method to provide real-time feedback and coaching to augment cardiac rescue by a rescuer. The rescuer would typically be attempting cardiopulmonary resuscitation (CPR) or administering an electrical shock from a defibrillator. The method includes a step of providing a computer configured for receiving an electromagnetic signal, such as from a camera, radar gun, or a microwave sensor. The computer is configured for using the electromagnetic signal to compute a distance of depression of a chest of the person in cardiac distress. The computer may be a stand-alone device or one that is integrated into other components used in the method.

The method includes a step of providing a data-generation device, such as a camera, a radar gun, or a microwave sensor. The data-generation device is connected to the computer so as to deliver data usable by the computer to compute the distance of depression of a chest of the person in cardiac distress. Using this information, the computer can also calculate the rate of depression and the number of depressions over a period of time.

The method includes a step of providing a cuing device capable of sending guidance to the rescuer. The cuing device is connected to the computer. So, when depth of compression and rates are calculated by the computer, the cuing device may be activated with CPR coaching on the proper depth and rate and may further recommend when to administer mouth to mouth breaths. Examples of a cuing device include a speaker, headphones, a cell phone and augmented reality glasses.

The method includes a step of using the data-generation device to provide data to the computer sufficient for the computer to track the distance of depression of the chest of the person in cardiac distress. The depression of the chest of the person being rescued can be measured directly by tracking the chest of the person being rescued, or measured indirectly by tracking the rescuer's hands while performing CPR.

The method includes a step of activating the cuing device to send a recommendation to the rescuer when an adjustment of an action of the rescuer is suggested by the computer in treating the person in cardiac distress. Optionally, augmented reality glasses may be part of the cuing device.

The method optionally includes a step of attaching an article to the rescuer. The term attaching is intended to include something worn by the rescuer such that the article moves with the rescuer. This article is used to help measure distance of chest compression when a camera is used as the data-generation device. The article is configured to be attached to the rescuer at or near a wrist of the rescuer, an example is a slap bracelet that can be quickly attached. The article displays a shape, such as an image or a physical shape that is visible to the camera after attachment to the rescuer.

The method optionally includes a step of providing a stationary component configured with a shape or image having known dimensions visible to the camera as an aid to the computer in calculating distance. The stationary component is used by the computer to compute a distance of depression of a chest of the person in cardiac distress. The known shape or image is detectable by the camera and then usable by the camera to calibrate the stationary component for use by the computer to track the distance of depression of the chest of the person in cardiac distress.

The method optionally includes a step of using the camera to provide data to the computer. The camera data is used by the computer to compute a distance of depression of a chest of the person in cardiac distress. The camera data is used by the computer in combination with data on a location of the stationary component and with data on any movement of the article at or near the wrist of the rescuer. The camera may be attachable to the rescuer and an inertial measurement unit may be integrated into the camera.

The method optionally includes a step of recording data from the use of a defibrillator configured for observation by the computer. This data includes the rate of cardio pulmonary resuscitation and depth of chest compression by the rescuer.

The method optionally includes a step of combining the data from the use of a defibrillator and the data on a rate of cardio pulmonary resuscitation and depth of chest compression by the rescuer with video data from the camera to produce combined data, which will be available for after-action review.

Technical Problem

A frequent challenge for untrained responders to a sudden cardiac arrest is helping them understand what to do, how to do it, and (sometimes as important) what not to do. Even trained first responders could find real time coaching helpful during an emergency.

Audio and video prompts, or even 911 assisted coaching, doesn't always provide the detail needed because real time data cannot be assessed. This can be especially problematic with cardio-pulmonary resuscitation (CPR), where rate and depth of compressions are particularly important (along with limiting pauses to that CPR).

Using existing methods for guiding proper placement of defibrillator pads on a patient can be deficient because there is no visual context in relation to the actual person in the environment nor any way to visually confirm correct pad placement.

While a modern defibrillators can be programmed to detect proper pad placement by measuring resistance between the pads, there is no way to automate visual validation of correct pad placement. Visual validation would also improve delivery of CPR because it can advise on best patient position, such as lying on a hard flat surface that also minimizes any water hazard that might pose a danger when using a defibrillator.

Existing CPR coaching devices do not effectively address leaning during CPR, which is a recognized problem. The National Institutes of Health published a report stating: "Leaning during CPR increases intrathoracic pressure, decreases coronary perfusion pressure, and decreases cardiac output and myocardial blood flow. Leaning is common during CPR."

Solution to Problem

The solution is a method that maximizes treatment efficacy using computer vision, inertial measurement unit technology, and positional GPS. Preferably, computer vision utilizes augmented reality glasses that would enable observation of the scene and further enable step by step instructions and real time feedback during a rescue.

Augmented reality glasses, such as GOOGLE GLASS or FACEBOOK'S PROJECT ARIA glasses can be supplemented with computer vision to overlay (via augmented reality) where defibrillator pads are supposed to go on the patient by showing the wearer with outlines on a person's body to indicate exactly where the defibrillator pads should be placed, or where to put their hands for CPR. In addition, the augmented reality glasses can be programmed to explicitly indicate to a rescuer when the defibrillator pads are in the wrong place. Using such a scheme, the "virtual outlines" of the pads might change color when the pads are correctly applied (e.g., green when applied correctly, red when not applied correctly, yellow when close). Auditory queues to help guide the responder are also possible.

The solution is using computer vision to identify dangerous conditions that may be present, such as the patient situated in water (or amid other environmental dangers); identifying if the patient is on a mattress or other soft surface that would preclude effective CPR; discovering if the patient is sufficiently hairy so as to preclude functioning or adherence of AED pads and if so to instruct the rescuer to shave the chest; to instruct the rescuer regarding removal of garments, which can be important if a rescuer is overly worried about patient dignity to the extent that time-critical therapy is not provided.

The solution is using real time CPR recording and feedback instructing the rescuer to push harder (depth), faster (rate), when to pause for a defibrillator shock (via integration with a defibrillator), and when to resume.

The solution uses computer vision, differential GPS, and data derived from hardware inertial measurement units to provide real time feedback to rescuers assisting with a cardiac arrest.

The solution is a system that provides recommendations by calculating and then instructing the rescuer to adjust for "leaning" during CPR.

BRIEF DESCRIPTION OF DRAWINGS

The drawings illustrate the steps in preferred embodiments of the method to provide real-time feedback and coaching to augment cardiac rescue according to the disclosure. Dashed lines in the drawings reflect optional steps in the method. If a step to be implemented is not explicitly or implicitly required prior to another step in the chart, then the step to be implemented may be performed in an order different from that charted.

DESCRIPTION OF EMBODIMENTS

In the following description, reference is made to the accompanying drawings, which form a part hereof and which illustrate several embodiments of the present invention. The drawings and the preferred embodiments of the invention are presented with the understanding that the present invention is susceptible of embodiments in many different forms and, therefore, other embodiments may be utilized and structural, and operational changes may be made, without departing from the scope of the present invention.

Figure 2:
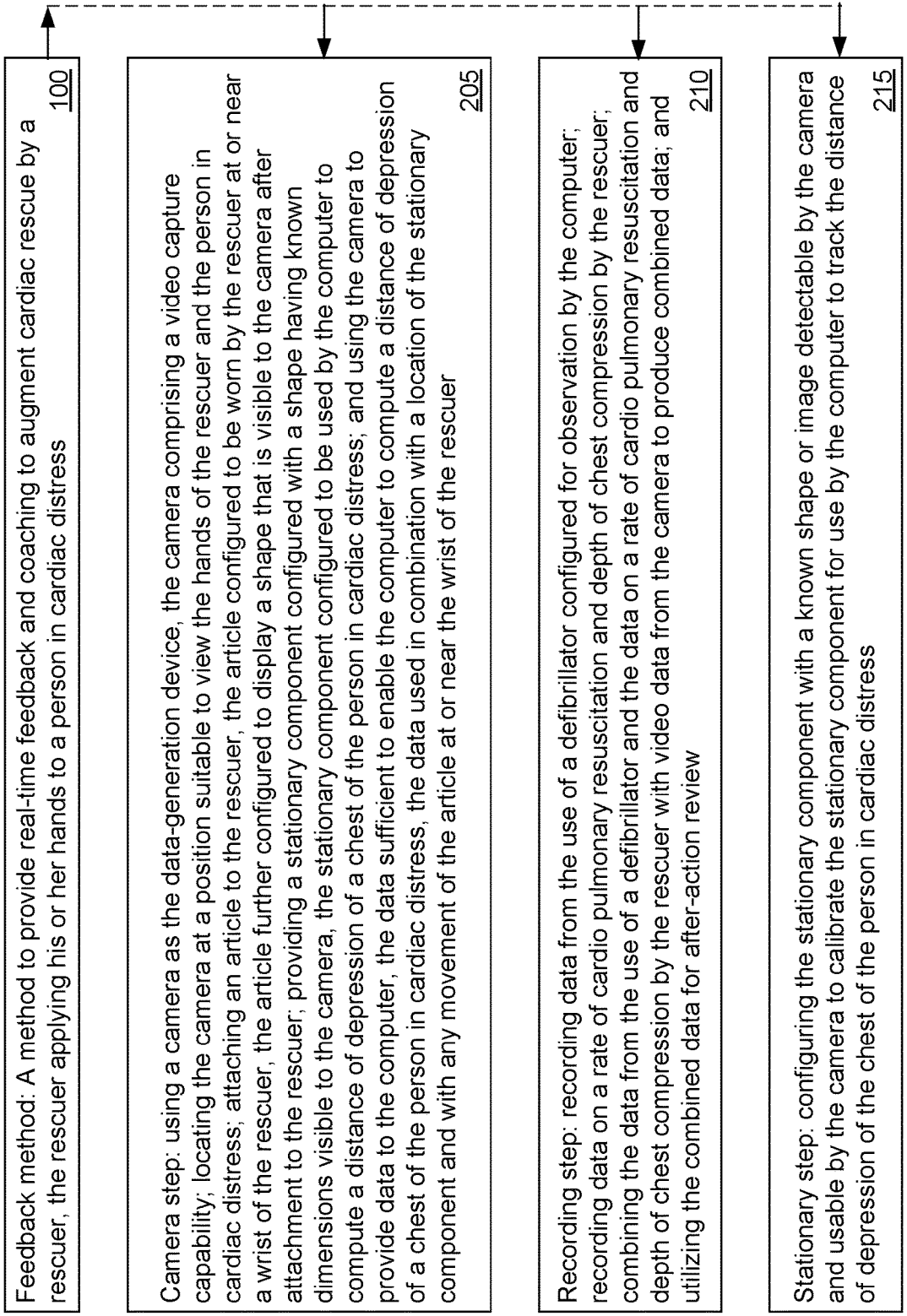
FIG. 2 is a chart illustrating optional added steps in the method.
Figure 3:
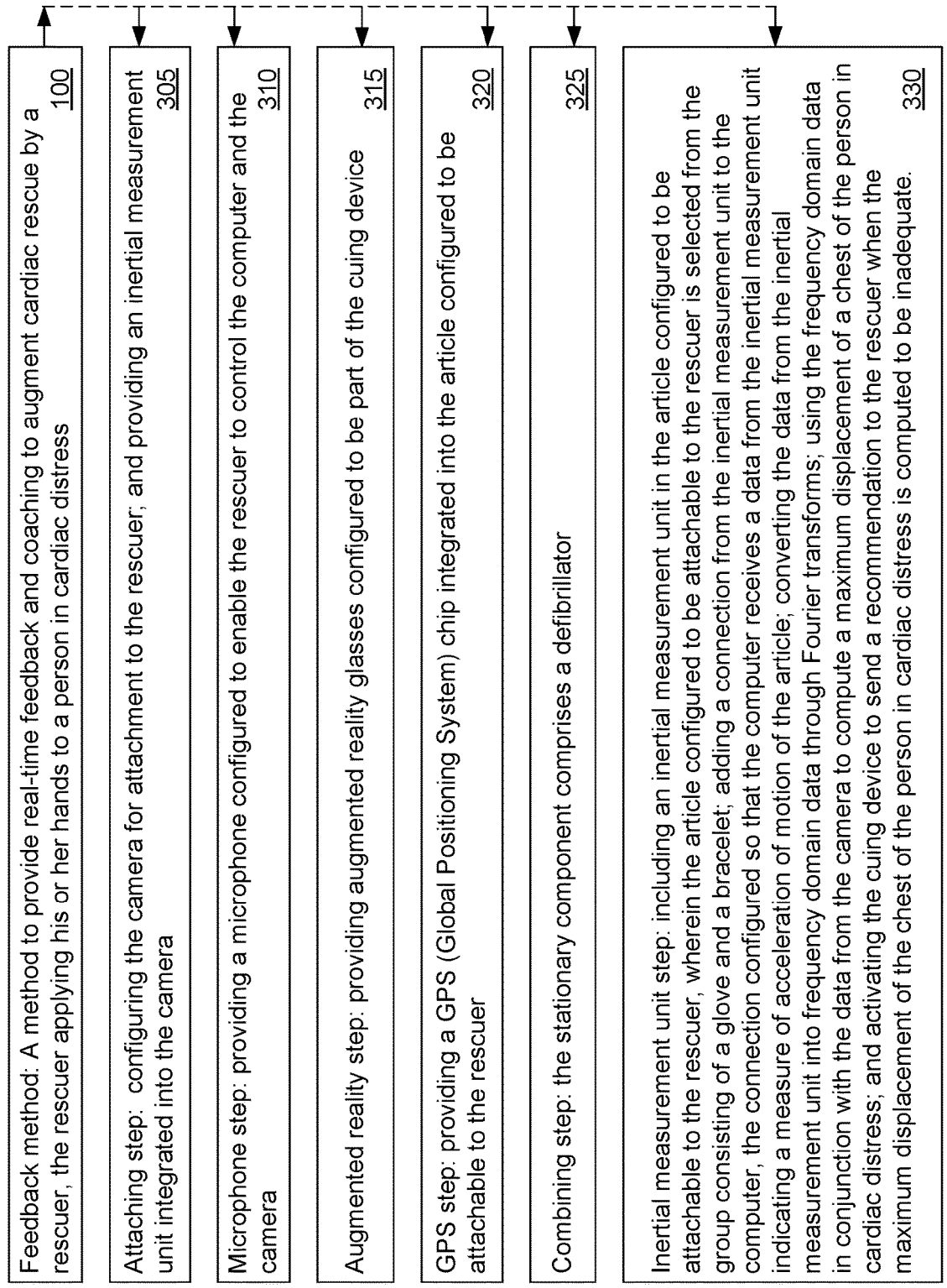
FIG. 3 is a chart illustrating optional added steps in the method.
Figure 4:
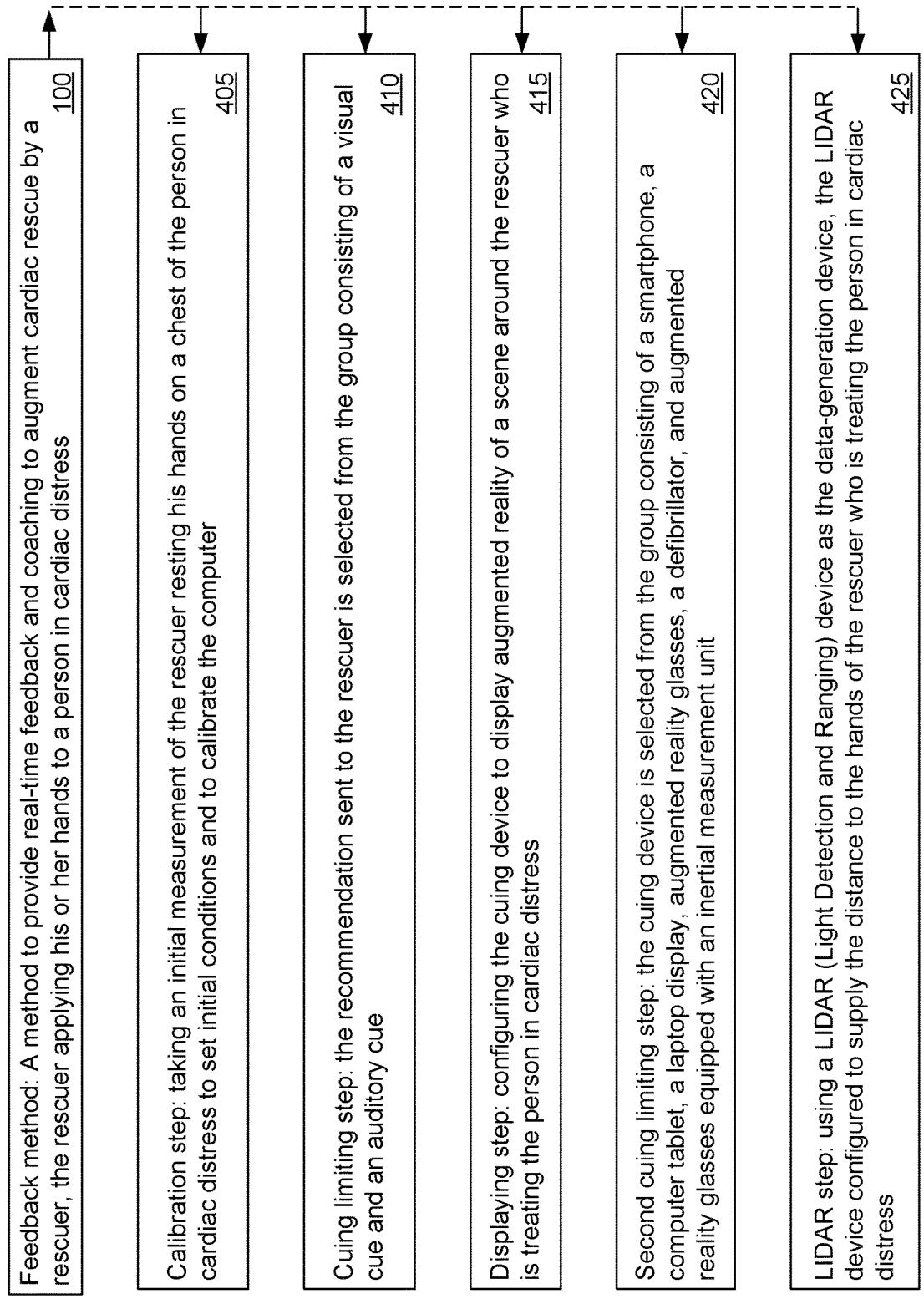
FIG. 4 is a chart illustrating optional added steps in the method.
Figure 5:
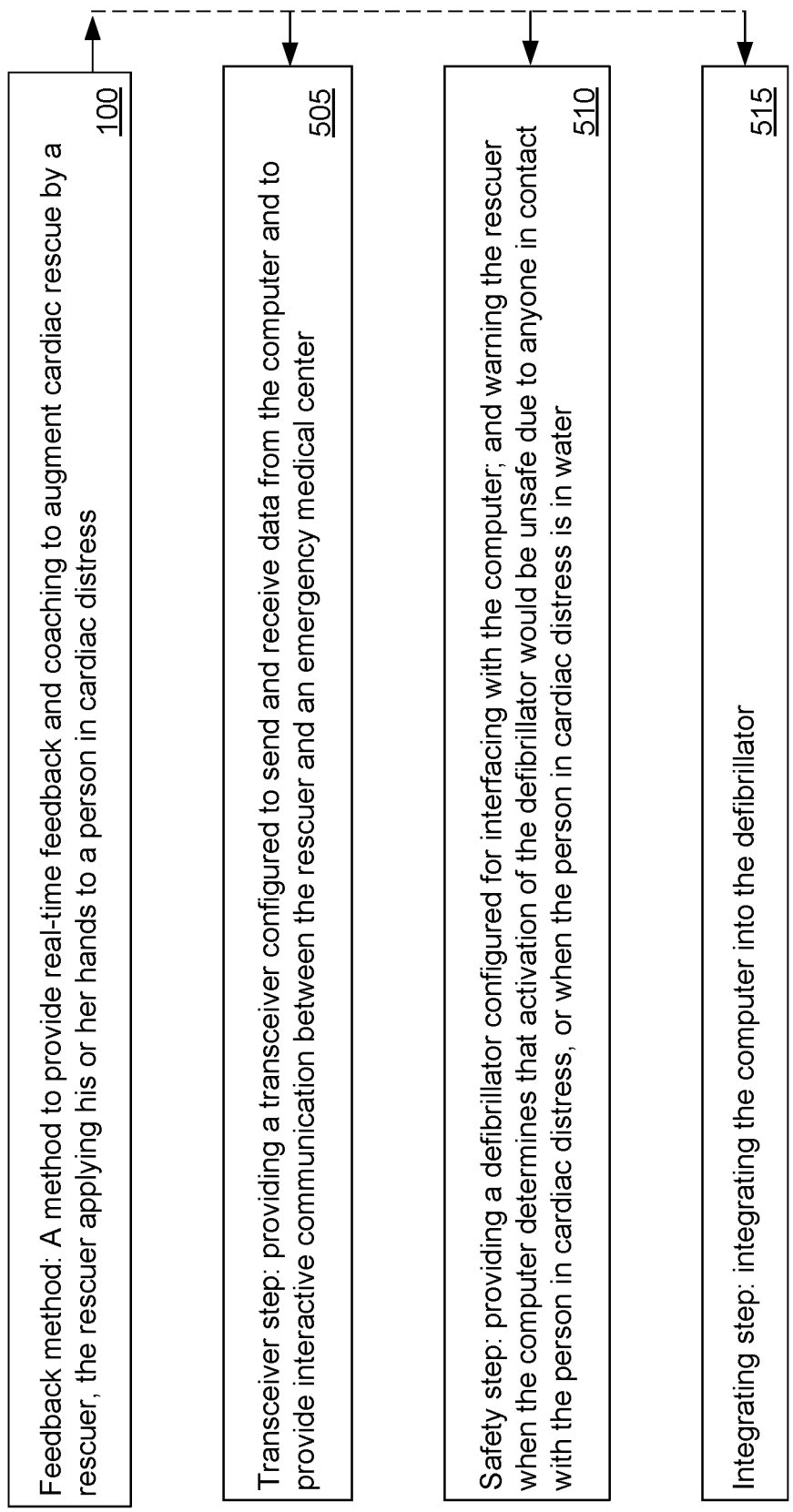
FIG. 5 is a chart illustrating optional added steps in the method.

The reference numbers in the drawings are used consistently throughout. New reference numbers in FIG. 2 are given the 200 series numbers. Similarly, new reference numbers in each succeeding drawing are given a corresponding series number beginning with the figure number. Thus, the reference numbers inherently disclose the figure in which they are first found.

Figure 1:
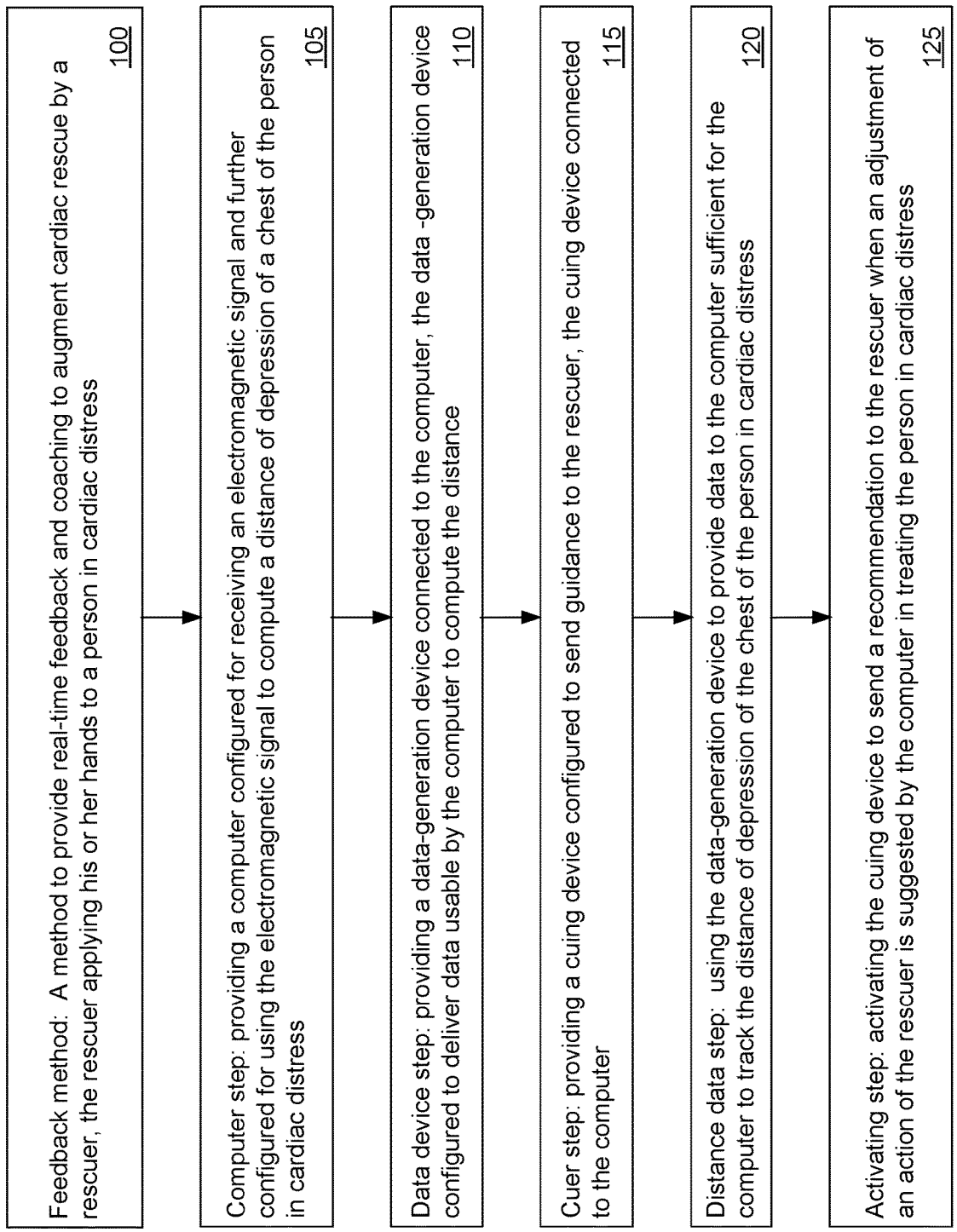
FIG. 1 is a flow chart illustrating required steps in the method to provide real-time feedback for a cardiac rescue.
Figure 6:
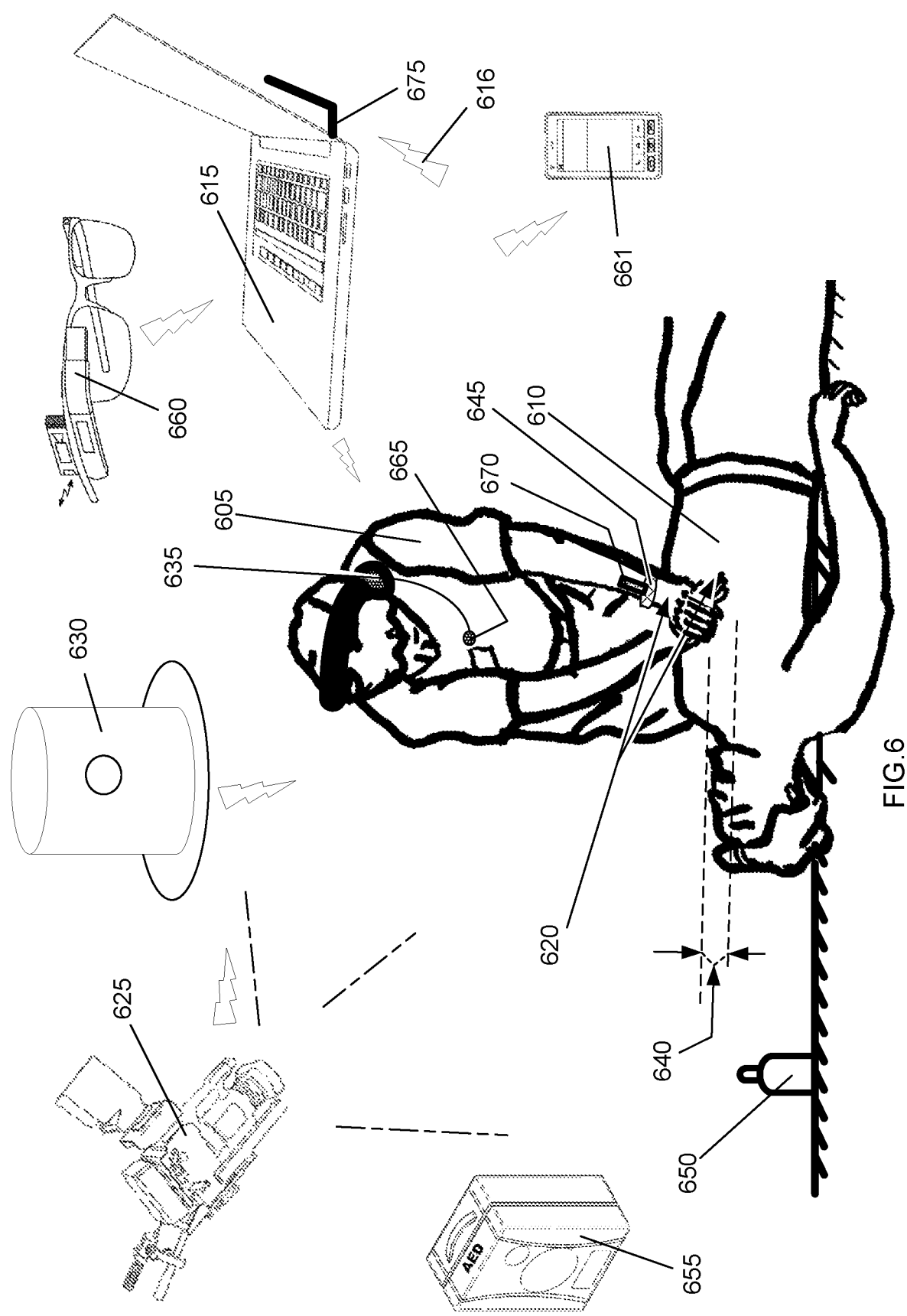
FIG. 6 is an illustration of a rescuer treating a person in cardiac arrest.

FIG. 1 is a chart illustrating steps in the method and FIG. 6 illustrates various components used in the method. The Feedback method (100) is a method to provide real-time feedback and coaching to augment cardiac rescue by a rescuer (605), the rescuer (605) applying his or her hands (620) to a person (610) in cardiac distress.

The Feedback method (100) includes a Computer step (105) that requires providing a computer (615) configured for receiving an electromagnetic signal (616) and further configured for using the electromagnetic signal (616) to compute a distance (640) of depression of a chest of the person (610) in cardiac distress.

The Feedback method (100) includes a Data device step (110) that involves providing a data-generation device connected to the computer (615), the data-generation device configured to deliver data usable by the computer (615) to compute the distance. Examples of a data-generation device include a camera (625), augmented reality glasses (660) and a LIDAR (630) (Light Detection and Ranging) device. The camera (625) can generate visual data that can be interpreted by the computer. The augmented reality glasses (660) can sense the field of view in front of the glasses and interact with the computer. Similarly, the LIDAR (630) device generates data on the scene that can be utilized by the computer to determine movement by persons or things within the scene being sensed.

The Feedback method (100) includes a Cuer step (115) that involves providing a cuing device capable of sending guidance to the rescuer (605), the cuing device connected to the computer (615). Examples of cuing devices would typically include a headphone (635), a cell phone (661), or a pair of augmented reality glasses (660).

The Feedback method (100) includes a Distance data step (120) that involves using the data-generation device to provide data to the computer (615) sufficient for the computer (615) to track the distance (640) of depression of the chest of the person (610) in cardiac distress.

The Feedback method (100) includes an Activating step (125) that involves activating the cuing device to send a recommendation to the rescuer (605) when an adjustment of an action of the rescuer (605) is suggested by the computer (615) in treating the person (610) in cardiac distress.

The Feedback method (100) optionally includes a Camera step (205). The Camera step (205) involves using a camera (625) as the data-generation device. The camera (625) comprises a video capture capability. The Camera step (205) includes locating the camera (625) at a position suitable to view the hands (620) of the rescuer (605) and the person (610) in cardiac distress. The Camera step (205) includes attaching an article (645) to the rescuer (605). The article (645) may be configured to be worn by the rescuer (605) at or near a wrist of the rescue. A traditional wrist band that pulls over the hand to rest at the wrist, or a more modern slap band that is quickly applied to the wrist are two examples. The article (645) is further configured to display a shape that is visible to the camera (625) after attachment to the rescuer (605).

The Camera step (205) includes providing a stationary component (650) configured with a shape having known dimensions visible to the camera (625). The stationary component (650) is configured to be used by the computer (615) to compute a distance (640) of depression of a chest of the person (610) in cardiac distress.

Finally, the Camera step (205) includes using the camera (625) to provide data to the computer (615). The data from the camera (625) is sufficient to enable the computer (615) to compute a distance (640) of depression of a chest of the person (610) in cardiac distress. The data from the camera (625) is used in combination with a location of the stationary component (650) and with any movement of the article (645) at or near the wrist of the rescuer (605).

The Feedback method (100) optionally includes a Recording step (210) that involves recording data from the use of a defibrillator (655) configured for observation by the computer (615). The defibrillator (655) may be an Automated External Defibrillator, or AED. The defibrillator (655) sends its operational data to the computer (615) for recording and for calculations performed by the computer (615). Examples of recording data include a rate of cardiopulmonary resuscitation from the defibrillator (655) or the computer, and computer-calculated depth of chest compression by the rescuer (605). The computer (615) is further configured to combine data from the use of a defibrillator (655) and the data on a rate of cardio pulmonary resuscitation and depth of chest compression by the rescuer (605) with video data from the camera (625) to produce combined data. One use for the combined data is for after-action review.

The Feedback method (100) optionally includes a Stationary step (215) that involves configuring the stationary component (650) with a known shape or image detectable by the camera (625) and usable by the camera (625) to calibrate the stationary component (650) for use by the computer (615) to track the distance (640) of depression of the chest of the person (610) in cardiac distress. Essentially, one calibrates the stationary component (650) by enabling use of the stationary component (650) as a fixed reference point.

The Feedback method (100) optionally includes an Attaching step (305) that involves configuring the camera (625) for attachment to the rescuer (605), and further involves providing an inertial measurement unit integrated into the camera (625). In this step, the camera (625) might be mounted on a headband or affixed to the rescuer's clothing.

The Feedback method (100) optionally includes a Microphone step (310) that involves providing a microphone (665) configured to enable the rescuer (605) to control the computer (615) and the camera (625). The microphone (655) may also be used to communicate with emergency first response via telecommunication.

The Feedback method (100) optionally includes an Augmented reality step (315) that involves providing augmented reality glasses (660) configured to be part of the cuing device.

The Feedback method (100) optionally includes a GPS step (320) that involves providing a GPS (Global Positioning System) chip integrated into the article (645) configured to be attachable to the rescuer (605). The GPS chip provides location and positioning data for use in the calculations performed by the computer (615).

The Feedback method (100) optionally includes a Combining step (325) that specifies that the stationary component (650) comprises a defibrillator (655). In this step, the defibrillator (655) or its case serves an ancillary purpose. As noted herein, other components may be combined whenever practical. Examples included combining the computer (615) with the article (645) and/or the stationary component (650).

The Feedback method (100) optionally includes an inertial measurement unit step (330) that involves including an inertial measurement unit (670) in the article (645) configured to be worn by the rescuer (605). In this step, the article (645) is configured to be attachable to the rescuer (605) is selected from the group consisting of a glove and a bracelet. Other possibilities are a sticker, an adhesive patch, a watch, or a ring.

An inertial measurement unit (330) includes an accelerometer, a gyroscope, and a magnetometer in one unit. An example of an inertial measurement unit would provide 3-axis data output (Pitch Roll Yaw) that includes acceleration plus gyroscope, plus angle, plus magnetic field, in a measurement range with a selectable output rate. The inertial measurement unit (670) could be a BLUETOOTH inertial measurement unit connected to the cell phone (661). Effectively, the inertial measurement unit (330) is measures 9 axes: 3 axes for acceleration, 3 for gyroscope, and 3 for magnetometer.

The Inertial measurement unit step (330) includes adding a connection from the inertial measurement unit to the computer (615). This connection is configured so that the computer (615) receives a data from the inertial measurement unit indicating a measure of acceleration of motion of the article (645).

The inertial measurement unit step (330) includes converting the data from the inertial measurement unit into frequency domain data through Fourier transforms and then using the frequency domain data in conjunction with the data from the camera (625) to compute a maximum displacement of a chest of the person (610) in cardiac distress. The inertial measurement unit step (330) finally includes activating the cuing device to send a recommendation to the rescuer (605) when the maximum displacement of the chest of the person (610) in cardiac distress is computed to be inadequate.

The Feedback method (100) optionally includes a Calibration step (405) that involves taking an initial measurement of the rescuer (605) resting hands (620) on a chest of the person (610) in cardiac distress to set initial conditions and to calibrate the computer (615).

The Feedback method (100) optionally includes a Cuing limiting step (410) limiting the recommendation sent to the rescuer (605) to one selected from the group consisting of a visual cue and an auditory cue.

The Feedback method (100) optionally includes a Displaying step (415) that requires configuring the cuing device to display augmented reality of a scene around the rescuer (605) who is treating the person (610) in cardiac distress The Feedback method (100) optionally includes a Second cuing limiting step (420) that requires selection of the cuing device from the group consisting of a smartphone, a computer (615) tablet, a laptop display, augmented reality glasses (660), a defibrillator (655), and augmented reality glasses (660) equipped with an inertial measurement unit (670). The augmented reality glasses (660) may include the computer (615).

The Feedback method (100) optionally includes a LIDAR step (425) that requires using a LIDAR (630) (Light Detection and Ranging) device as the data-generation device. The LIDAR (630) device is configured to supply the distance to the hands or the chest (620) of the rescuer (605) who is treating the person (610) in cardiac distress. Alternatively, the article (645), such as a sticker, may be attached the chest of the person (610) in cardiac distress.

The Feedback method (100) optionally includes a Transceiver step (505) that requires providing a transceiver (675) configured to send and receive data from the computer (615) and to provide interactive communication between the rescuer (605) and an emergency medical center. The transceiver is an electronic device which is a combination of a radio transmitter and a receiver. The transceiver can both transmit and receive radio waves using an antenna for communication purposes.

The Feedback method (100) optionally includes a Safety step (510) that includes providing a defibrillator (655) configured for interfacing with the computer (615). The Safety step (510) further includes warning the rescuer (605) when the computer (615) determines that activation of the defibrillator (655) would be unsafe due to anyone in contact with the person (610) in cardiac distress, or when the person (610) in cardiac distress is in water.

The Feedback method (100) optionally includes an Integrating step (515) that provides for integrating the computer (615) into the defibrillator (655). This step is instructive in that, whenever practical, any component used in the method of the invention can be combined with any other component to perform multiple functions.

EXAMPLE

In this example, the method employs a computer capable of processing vision, a camera wirelessly connected to the computer, a device capable of providing visual cues, auditory cues and augmented reality of a scene with a person in need of cardiac rescue and a rescuer. In this example the augmented reality glasses have an inertial measurement unit, an integrated camera, a computer, and a speaker.

In this example, the method further employs a bracelet or wrist band which contains an image of known size that is used to determine the distance between the camera and rescuer's hands. The wrist band also contains a GPS chip.

In this example, the method further employs a stationary component, which is a small puck that sits on the ground next to the person in need of rescue. The puck has a known size and shape recognizable by the computer when viewed by the camera.

In this example, the augmented reality glasses provide visual cues, auditory instructions, real time feedback, and augmented reality to the rescuer wearing the augmented reality glasses.

In this example, a stationary GPS component is part of a defibrillator brought by the rescuer and is present at the scene.

In this example a rescuer is called to the scene of a person in need of cardiac rescue who is lying on the ground.

The rescuer dons the augmented reality glasses, which assess the situation via computer vision. Using video and audio queues the computer instructs the rescuer to yell at the person and shake them: "Are you okay? ARE YOU OKAY"? The inertial measurement unit in the glasses tracks the motion of the camera attached to the rescuer.

When the person does not respond, the augmented reality glasses receive instructions from the computer and provide audio instructions to the rescuer to put on a wrist band.

The augmented reality glasses receive further audio for the the rescuer to turn on the defibrillator. The computer next instructs the rescuer through the augmented reality glasses on what to do with real time feedback (e.g., placing pads, avoiding hazards etc.). This first instructions include CPR. CPR is the most complicated since the components must enable the computer to provide immediate feedback to the rescuer on rate, depth, and position. The computer is configured to tell the rescuer when to pause and when to resume CPR treatment.

The stationary component, the puck, is on the ground next to the patient. The defibrillator may also double as a stationary component. The augmented reality glasses provide receive visual and/or audio cues from the computer and instruct the rescuer to put on the rescue bracelet.

The computer sends instructions to the rescuer explaining the steps in implementing CPR. Through integration with the defibrillator, the computer tells the rescuer whether or not a shockable rhythm has been detected, whether or not to stop CPR, when to apply defibrillator pads, when to re-start CPR once pads are on, when to stop in order to shock, and when to start again. Using the camera, the computer confirms that no one is touching the patient before delivering any therapy and warns the rescuer if someone is touching the person in cardiac distress.

The computer assesses the visual data to determine the rate of CPR using the image of known size on the rescue bracelet and the stationary component. The computer assesses the change in height over time of the rescuer's hands and is confirmed using the inertial measurement unit and differential GPS between the GPS chip in the stationary puck and the GPS in the rescue bracelet.

CPR depth is calculated using an algorithm to combine the following calculations mathematically: Using only an inertial measurement unit on the bracelet the system measures the acceleration signal. This signal is then converted into the frequency domain through Fourier transforms. Using the frequency domain data, computer calculates average displacement without integration by modeling the displacement signal and computing the maximum displacement over the frequency.

The computer calculates where the rescuer's hands are in space above the floor. The computer determines how far away the glasses, which have the camera (625) incorporated therein, are from the person in cardiac distress by calibrating distance using the sensor in the bracelet and the stationary component. The computer determines the orientation of the rescuer's head using the inertial measurement unit built into the glasses.

The depth of the compression is computed by using differential GPS. Differential GPS uses data from the sensor in the wristband and stationary object. The computer then determines the Z axis motion.

The computer also determines the compression depth substituting vision for the GPS. By placing a puck or AED on the floor with an image of known size and within the line of sight of the camera in the augmented reality glasses, the computer: (1) computes the distance from the camera to stationary object then (2) computes the distance from the camera to the wristband. Subtracting those distances computes the height above the floor of the rescuer's hands or patient's chest. Using this data, the camera uses video to calculate, and coach, the rescuer to perform CPR at the proper depth and rate.

The above-described embodiments including the drawings are examples of the invention and merely provide illustrations of the invention. Other embodiments will be obvious to those skilled in the art. Thus, the scope of the invention is determined by the appended claims and their legal equivalents rather than by the examples given.

INDUSTRIAL APPLICABILITY

The invention has application to the rescue industry.

What is claimed is:

1. A method to provide real-time feedback and coaching to augment cardiac rescue by a rescuer, the rescuer applying his or her hands to a person in cardiac distress, the method comprising the steps of:
   providing a computer, a stationary component, a data-generation device, an article, and a cuing device;
   configuring the computer to receive data from the data-generation device;
   locating the data-generation device to view the stationary component and the article;
   configuring the stationary component as a fixed reference, the stationary component comprises a defibrillator and is further configured with a shape or image having a known dimension;
   attaching the article to be movable with a chest of the person in cardiac distress, the article configured with a shape or image having a known dimension;
   viewing the article and the stationary component with the data-generation device to generate the data sent to the computer;
   operating the computer for calculation of a movement of the article over time relative to the stationary component, said calculation comprising a determination of the difference between a first distance and a second distance, said first distance defined by the space between the data-generation device and the stationary component and calculated using the data and the known dimension of the stationary component, said second distance defined by the space between the article and the data-generation device and calculated using the data and the known dimension of the article;
   configuring the cuing device to send guidance to the rescuer, the cuing device connected to the computer; and
   activating the cuing device to send a recommendation to the rescuer when an adjustment of an action of the rescuer is suggested by the computer in treating the person in cardiac distress.

2. The method of claim 1, further comprising the steps of:
   recording defibrillator data from the use of the defibrillator, the defibrillator configured for observation by the data-generation device;
   recording the data from the data-generation device on a rate of cardio pulmonary resuscitation and depth of chest compression by the rescuer;
   combining the defibrillator data from the use of a defibrillator and the data from the data-generation device on the rate of cardio pulmonary resuscitation and depth of chest compression by the rescuer to produce combined data; and
   utilizing the combined data for after-action review.

3. The method of claim 1, further comprising the step of providing a microphone configured to enable the rescuer to control the computer and the data-generation device.

4. The method of claim 1, further comprising the step of providing augmented reality glasses configured to be part of the cuing device.

5. The method of claim 1, further comprising the step of providing a GPS (Global Positioning System) chip integrated into the article configured to be attachable to the rescuer.

6. The method of claim 1, further comprising the steps of:
   including an inertial measurement unit in the article configured to be attachable to the rescuer;
   adding a connection from the inertial measurement unit to the computer, the connection configured so that the computer receives motion data from the inertial measurement unit indicating a measure of acceleration of motion of the article;
   converting the motion data from the inertial measurement unit into frequency domain data through Fourier transforms;
   using the frequency domain data in conjunction with the data from the data-generation device to compute a maximum displacement of a chest of the person in cardiac distress; and
   activating the cuing device to send a recommendation to the rescuer when the maximum displacement of the chest of the person in cardiac distress is computed to be inadequate.

7. The method of claim 1, wherein the recommendation sent to the rescuer is selected from the group consisting of a visual cue and an auditory cue.

8. The method of claim 1, further comprising the step of configuring the cuing device to display augmented reality of a scene around the rescuer who is treating the person in cardiac distress.

9. The method of claim 1, wherein the cuing device is selected from the group consisting of a smartphone, a computer tablet, a laptop display, augmented reality glasses, a defibrillator, and augmented reality glasses equipped with an inertial measurement unit.

10. The method of claim 1, further comprising the step of providing a microphone configured to enable the rescuer to interact with the computer, whorl the computer configured is with artificial intelligence.

11. The method of claim 1, further comprising the step of providing a transceiver configured to send and receive data from the computer and to provide interactive communication between the rescuer and an emergency medical center.

12. The method of claim 1, further comprising the steps of:
   the defibrillator being configured for interfacing with the computer; and
   warning the rescuer when the computer determines that activation of the defibrillator would be unsafe due to anyone in contact with the person in cardiac distress, or when the person in cardiac distress is in water.

13. The method of claim 12, further comprising the step of integrating the computer into the defibrillator.

\* \* \* \* \*